United States Patent
Muramoto

(10) Patent No.: US 10,594,874 B2
(45) Date of Patent: Mar. 17, 2020

(54) MALFUNCTION DETERMINING APPARATUS, MALFUNCTION DETERMINING SYSTEM, MALFUNCTION DETERMINING METHOD, AND RECORDING MEDIUM

(71) Applicant: RICOH COMPANY, LTD., Tokyo (JP)

(72) Inventor: Yohsuke Muramoto, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 15/401,586

(22) Filed: Jan. 9, 2017

(65) Prior Publication Data

US 2017/0208183 A1    Jul. 20, 2017

(30) Foreign Application Priority Data

Jan. 15, 2016 (JP) .................................. 2016-006679
Nov. 14, 2016 (JP) .................................. 2016-221929

(51) Int. Cl.
| | |
|---|---|
| G06F 15/00 | (2006.01) |
| H04N 1/00 | (2006.01) |
| H04N 1/32 | (2006.01) |
| G01N 29/14 | (2006.01) |
| G01P 15/00 | (2006.01) |

(52) U.S. Cl.
CPC ......... *H04N 1/00029* (2013.01); *G01N 29/14* (2013.01); *G01P 15/00* (2013.01);
(Continued)

(58) Field of Classification Search
CPC ........... H04N 1/00029; H04N 1/00015; H04N 1/00039; H04N 1/00058; G01N 29/14; G01P 15/00
(Continued)

(56) References Cited

U.S. PATENT DOCUMENTS

| | | | |
|---|---|---|---|
| 5,473,315 A | 12/1995 | Holroyd | |
| 2014/0054839 A1 | 2/2014 | Umi et al. | |
| 2016/0147187 A1 | 5/2016 | Muramoto et al. | |

FOREIGN PATENT DOCUMENTS

| | | |
|---|---|---|
| EP | 2 701 375 A2 | 2/2014 |
| EP | 2 701 375 A3 | 2/2014 |

(Continued)

OTHER PUBLICATIONS

Extended European Search Report dated Jul. 11, 2017 in Patent Application No. 17150932.6.
(Continued)

*Primary Examiner* — Mark R Milia
(74) *Attorney, Agent, or Firm* — Xsensus LLP

(57) ABSTRACT

A malfunction determining apparatus for determining a malfunction of a target apparatus includes a receiver that receives, from a target apparatus, a plurality of items of physical data having frequency bands that are different from each other and circuitry that analyzes the received physical data to identify, for each of the operating modes, at least one of the physical data items having a specific feature from among the plurality of items of physical data that are received from the target apparatus, stores in a memory, for each of the operating modes, information indicating at least one sensor of the multiple sensors that has output the at least one of the physical data item that is identified, and determines abnormality of the target apparatus operating in a specific operating mode, using only the physical data output from the at least one sensor stored in the memory for the specific operating mode.

9 Claims, 10 Drawing Sheets

(52) U.S. Cl.
CPC ....... *H04N 1/00002* (2013.01); *H04N 1/0005* (2013.01); *H04N 1/00015* (2013.01); *H04N 1/00039* (2013.01); *H04N 1/00058* (2013.01); *H04N 1/00063* (2013.01); *H04N 1/00477* (2013.01); *H04N 1/3263* (2013.01); *H04N 1/32657* (2013.01)

(58) Field of Classification Search
USPC ........................................................ 358/1.14
See application file for complete search history.

(56) References Cited

FOREIGN PATENT DOCUMENTS

| | | |
|---|---|---|
| GB | 2 282 224 A | 3/1995 |
| JP | 2007-051952 | 3/2007 |
| JP | 2010-054558 | 3/2010 |
| JP | 2016-105267 | 6/2016 |

OTHER PUBLICATIONS

Nishchal K. Verma, et al., "Smartphone Application for Fault Recognition" Sensing Technology (ICST), 2012 Sixth International Conference on, IEEE, XP032425481, Dec. 18, 2012, pp. 629-634.

N. Tandon, et al., "A Review of Vibration and Acoustic Measurement Methods for the Detection of Defects in Rolling Element Bearings" Tribology International, vol. 32, No. 8, XP002237398, Jan. 1, 1999, pp. 469-480.

Stephen V Rice, et al., "General-Purpose Real-Time Monitoring of Machine Sounds" Essential Technologies for Successful Prognostics: Proceedings of the 59th Meeting of the Society for Machinery Failure Prevention Technology, XP055383114, Apr. 21, 2005, pp. 545-549.

MALFUNCTION DETERMINING APPARATUS, MALFUNCTION DETERMINING SYSTEM, MALFUNCTION DETERMINING METHOD, AND RECORDING MEDIUM

CROSS-REFERENCE TO RELATED APPLICATION

This patent application is based on and claims priority pursuant to 35 U.S.C. § 119(a) to Japanese Patent Applications No. 2016-006679, filed on Jan. 15, 2016 and No. 2016-221929, filed on Nov. 14, 2016 in the Japan Patent Office, the entire disclosure of which is hereby incorporated by reference herein.

BACKGROUND

Technical Field

The present invention relates to a malfunction determining apparatus, a malfunction determining system, a malfunction determining method, and a non-transitory recording medium storing a malfunction determining program.

Background Art

The apparatuses that include loads driven by motors etc. such as image forming apparatuses, detect abnormality in operation by using audio-frequency signals (i.e., sound data from 20 Hz up to around 20 KHz). However, the frequency band used by such apparatuses is narrow, and a signal having a frequency band that can effectively improve precision in detecting abnormality is not used. For example, some apparatuses detect abnormality using sound collected by a condenser microphone, which is audio-frequency signals, to enhance safety of the image forming apparatus.

SUMMARY

Example embodiments of the present invention provide a novel malfunction determining apparatus for determining a malfunction of a target apparatus that includes a receiver that receives, from a target apparatus, a plurality of items of physical data having frequency bands that are different from each other, the physical data items being output by multiple sensors in the target apparatus while the target apparatus is operating in each one of a plurality of operating modes and circuitry that analyzes the received physical data to identify, for each of the operating modes, at least one of the physical data items having a specific feature from among the plurality of items of physical data that are received from the target apparatus, stores in a memory, for each of the operating modes, information indicating at least one sensor of the multiple sensors that has output the at least one of the physical data item that is identified, and determines abnormality of the target apparatus operating in a specific operating mode of the operating modes, using only the physical data output from the at least one sensor stored in the memory for the specific operating mode.

Further example embodiments of the present invention provide a malfunction determining system, a method of determining malfunction, and a non-transitory recording medium storing a malfunction determining program.

BRIEF DESCRIPTION OF THE DRAWINGS

A more complete appreciation of the disclosure and many of the attendant advantages thereof will be readily obtained as the same becomes better understood by reference to the following detailed description when considered in conjunction with the accompanying drawings.

Figure 1:
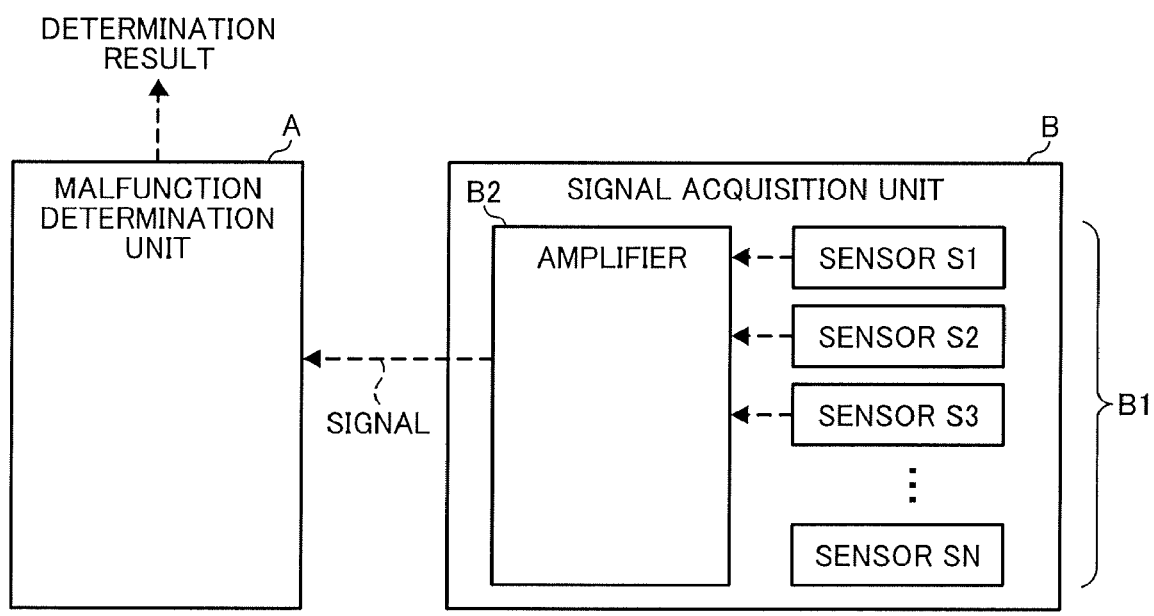
FIG. 1 is a schematic diagram illustrating a configuration of a malfunction determining apparatus as an embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

A more complete appreciation of the disclosure and many of the attendant advantages thereof will be readily obtained as the same becomes better understood by reference to the following detailed description when considered in conjunction with the accompanying drawings.

Embodiments of the present invention are described below in detail with reference to figures. In figures, same symbols are assigned to same or corresponding parts, and their descriptions are simplified or omitted appropriately.

Next, a basic configuration of a malfunction determining apparatus in this embodiment is described below.

FIG. 1 is a diagram illustrating a configuration of a malfunction determining apparatus in this embodiment.

As illustrated in FIG. 1, the abnormality determining apparatus includes a malfunction determination unit (determining unit) A and a signal acquisition unit B.

The signal acquisition unit B includes multiple sensors B1 (sensors S1 to SN) and an amplifier B2. After receiving signals from the sensors B1, which are amplified by an amplifier B2, the malfunction determination unit A determines whether or not the signals reflect abnormality.

Depending on circumstances, one or more of the sensors S1 to SN that collect sound data whose bands are different from each other are available. In this embodiment, three sensors, that is, a condenser microphone (whose frequency band is 20 Hz to 12 KHz, referred to as a sensor S1 hereinafter), an acceleration sensor (whose frequency band is 12 KHz to 30 KHz, referred to as a sensor S2 hereinafter), and an acoustic emission (AE) sensor (whose frequency band is 30 KHz to 1 MHz, referred to as a sensor S3 hereinafter), are used as an example.

It should be noted that each of sensors S1 to S3 may respectively acquire one-dimensional waveforms whose frequency bands are different from each other. It is assumed that the sensors S1 to S3 are included in an apparatus as a target to be measured ("target apparatus") and acquire sound data generated when the measured apparatus operates.

Next, an example case that the malfunction determining apparatus as described above is applied to the image forming apparatus is described below.

In this case, first, the image forming apparatus is described below.

Figure 2:
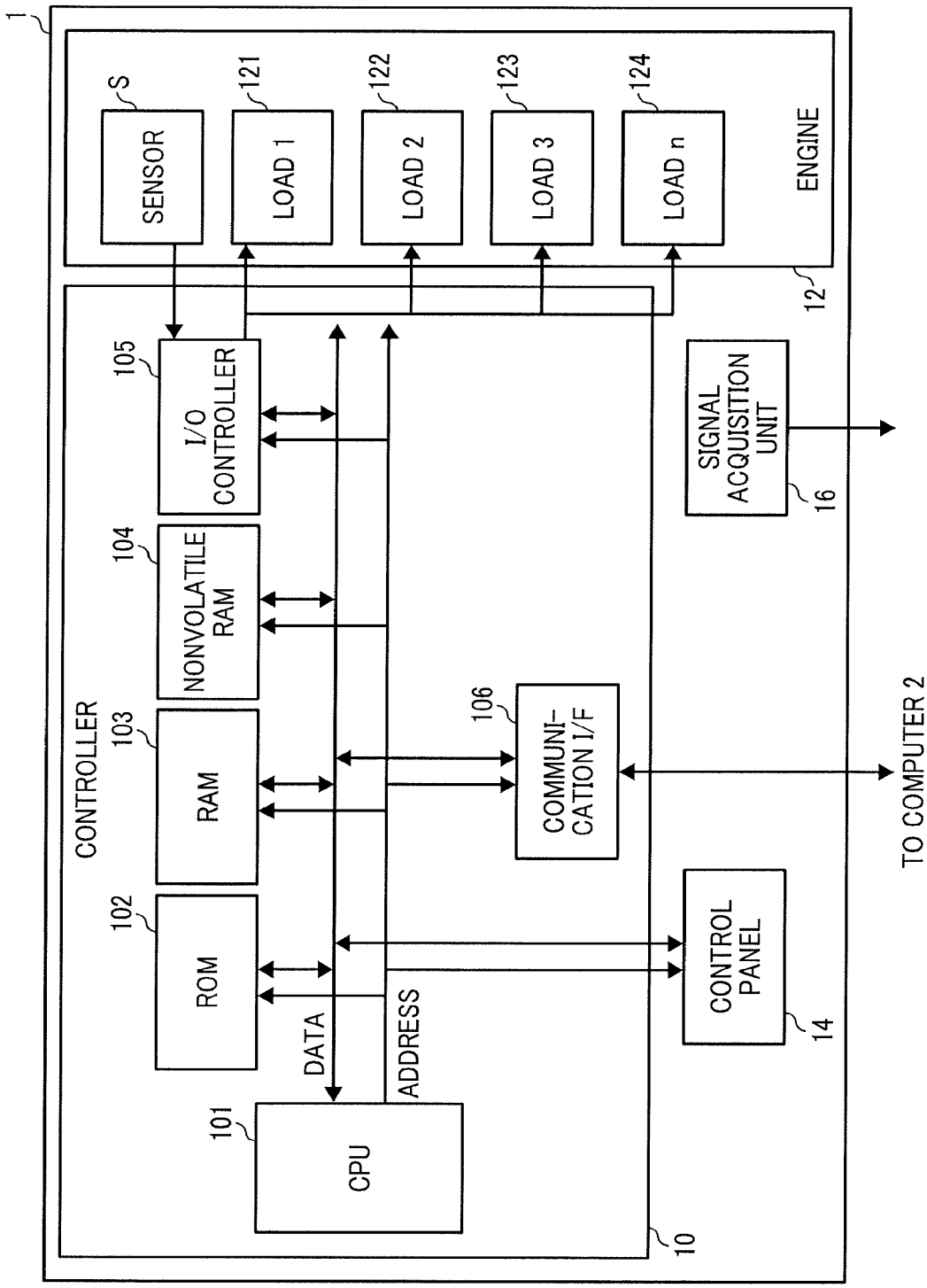
FIG. 2 is a schematic block diagram illustrating a configuration of an image forming apparatus as an embodiment of the present invention.

FIG. 2 is a block diagram illustrating a schematic configuration of the image forming apparatus 1 in this embodiment.

As illustrated in FIG. 2, the image forming apparatus 1 includes a controller 10, an engine 12, a control panel 14, and a signal acquisition unit 16.

The controller 10 includes a central processing unit (CPU) 101, a read only memory (ROM) 102 that stores a program for operating the CPU 101, a random access memory (RAM) 103 that provides a work area for the CPU 101 in executing the program, a nonvolatile RAM 104 that stores adjustment values for control and timing etc. and registered copy mode settings in a manner such that the data is kept even after the power is turned off, an input/output (I/O) controller 105 that controls loads (from 1 to n) in the engine 12 etc. based on inputs from sensors included in the engine 12 of the image forming apparatus 1, and a communication interface (I/F) 106 that communicates with a computer 2 (described later with reference to FIGS. 3 and 4) that is connected to the image forming apparatus 1.

The engine 12 forms an image and outputs the formed image.

The control panel 14 accepts a command input to the image forming apparatus 1 by user operation and displays an operating status of the image forming apparatus 1.

The signal acquisition unit 16 is located near loads (1 to n) 121 to 124 in the engine 12, acquires operating sound, and outputs data of the operating sound to the connected computer 2.

Figure 3:
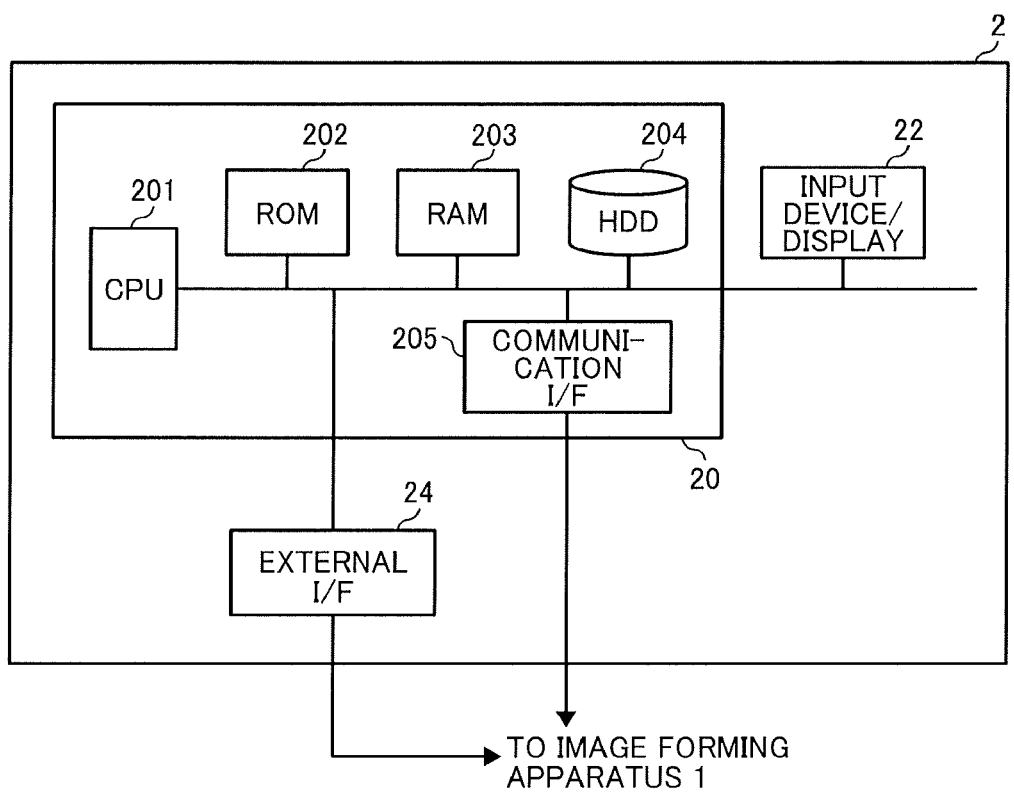
FIG. 3 is a schematic block diagram illustrating a configuration of a computer that determines abnormality as an embodiment of the present invention.

FIG. 3 is a block diagram illustrating a configuration of the computer 2 that determines abnormality in this embodiment.

As illustrated in FIG. 3, the computer 2 includes a controller 20 and a signal processor.

The controller 20 includes a CPU 201, a ROM 202 that stores a program for operating the CPU 201, the RAM 203 that provides a work area for the CPU 201 in executing the program, a hard disk drive (HDD) 204 that may keep data even after the power is turned off, a communication I/F 205 that communicates with the communication I/F 106 (illustrated in FIG. 2) in the image forming apparatus 1, and an input device/display 22 that accepts a command input to the computer 2 by user operation and displays a result of determining abnormality etc.

The signal processor communicates with a signal acquisition unit 16 (i.e., sensors S1 to S3) located inside the image forming apparatus 1 and includes an external I/F 24 that adjusts a level of the operating sound (analog signal) of the image forming apparatus 1 acquired by the signal acquisition unit 16 and converts the analog signal into a digital signal etc.

Figure 4:
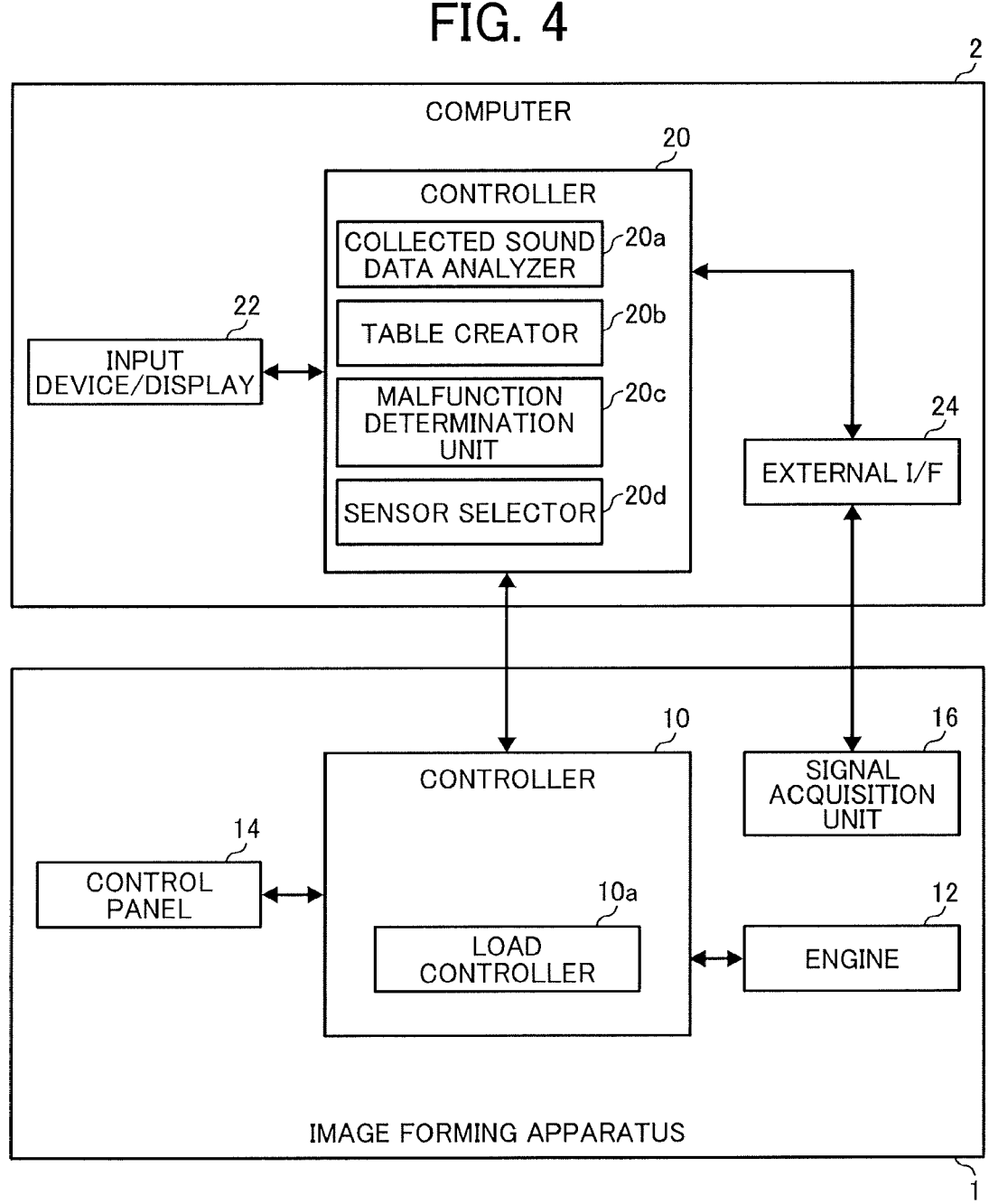
FIG. 4 is a diagram illustrating a malfunction determining system including the image forming apparatus and the malfunction determining apparatus (computer) as an embodiment of the present invention.

FIG. 4 is a diagram illustrating a malfunction determining system including the image forming apparatus 1 and a malfunction determining apparatus (i.e., the computer 2 in this case) in this embodiment.

In FIG. 4, regarding the image forming apparatus 1, only a part of the hardware configuration in FIG. 2 is illustrated. Similarly, regarding the computer 2, only a part of the configuration in FIG. 3 is illustrated.

A load controller 10a in the controller 10 is a functional unit implemented by operating the CPU 101 in the controller 10 using the program. Likewise, a collected sound data analyzer 20a, a table creator 20b, a malfunction determination unit 20c, and a sensor selector 20d are functional units implemented by operating the CPU 201 in the controller 20 using the program.

In accordance with a selection of the operating mode in the computer 2, the load controller 10a controls driving loads (1 to n) in the engine 12 for example. The collected sound data analyzer 20a commands to collect sound and performs frequency analysis on the collected sound data. The table creator 20b generates a table that indicates a relationship between the operating mode and the selected sensor (in addition, used frequency band) based on the frequency analysis on the collected sound data. The malfunction determination unit 20c determines whether or not the collected sound data reflects abnormality. As described later, the sensor selector 20d selects one sensor among multiple types of sensors whose frequency bands of the collected sound data are different with each other.

Here, the controller 10 in the image forming apparatus 1 and the controller 20 in the computer 2 are connected with each other via the respective communication control I/Fs 106 and 205.

The signal acquisition unit 16 in the image forming apparatus 1 is connected to the controller 20 via the external I/F 24 in the computer 2 and located near the loads (1 to n) in the engine 12 in the image forming apparatus 1 as described before to acquire the operating sound using the sensor S and outputs the data of the operating sound to the computer 2 via the external I/F 24 as a receiver.

The computer 2 analyzes the data of the operating sound collected by using the collected sound data analyzer 20a. After performing frequency analysis on the data in this case, the table creator 20b generates a table (described later). The malfunction determination unit 20c determines whether or not the loads (1 to n) operate abnormally based on the data of the operating sound (e.g., by comparing with the data of normal operating sound).

Next, a method of detecting abnormality by the image forming apparatus 1 is described below.

In this embodiment, any desired known technology is used for detecting abnormality. That is, the frequency values are plotted in the horizontal axis, and a strength of the sound data at each frequency value is plotted in the vertical axis. Subsequently, variation (i.e., difference) between a normal condition and an abnormal condition is considered. Furthermore, if the integral value of the variation exceeds a predetermined threshold value (that is, sound becomes louder or quieter), it is determined that the data reflects abnormality. However, other methods may be applied, such as the method of acquiring integral data across the frequency band to determine whether or not the data reflects abnormality, or the method of determining whether or not the data reflects abnormality in a comprehensive manner using individual determination results for each frequency band.

In this embodiment, three sensors S1 to S3 that collect sound data whose frequency bands are different with each other are used. The most effective sensor S is selected among the three sensors to determine whether or not the data reflects abnormality by using the signal acquired from that sensor S only. This increases accuracy in determination compared to a case of using signals acquired from all sensors S1 to S3.

That is, in comparing the signal reflecting the normal operation with the signal reflecting the abnormal operation across frequency bands, it is considered that there is no difference regarding the feature amount in most frequency bands. As a result, by using information of all frequency bands, information unnecessary for determining abnormality (i.e., noise in this case) is substantially mixed. Therefore, S/N ratio decreases, and precision in determining abnormality is lowered.

By contrast, if unnecessary information is not used, S/N ratio increases such that the precision in determining abnormality improves. Here, the reason for using multiple sensors and selecting one sensor among the multiple sensors, instead of using only one sensor from the start, is that it is preliminarily unknown which of the sensor outputs the signal that can be effectively used.

Therefore, the collected sound data analyzer 20a in the computer 2 preliminarily analyzes the signal output from each of the sensors S1 to S3 in operating the image forming apparatus 1 in a predetermined operating mode. In that case, by using a debug mode of the image forming apparatus 1, the computer 2 specifies a detailed operation to be performed by the image forming apparatus 1 through selecting a mode that drives a motor 1 only (hereinafter referred to as operating mode 1) and a mode that drives a motor 2 only (hereinafter referred to as operating mode 2) etc.

Based on a command input via the input device/display 22 by user operation, the computer 2 requests the image forming apparatus 1 to operate in the operating mode 1 via the communication I/F 205. Subsequently, in operating the image forming apparatus 1 in operating mode 1, the computer 2 stores sound data of the motor 1 acquired by the signal acquisition unit 16 in the HDD 204 as normal data.

Figure 5A:
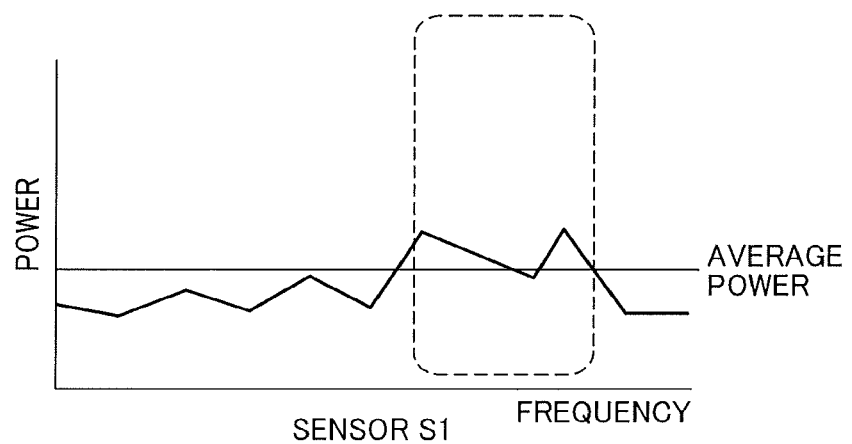
FIGS. 5A, 5B, and 5C are charts illustrating relationships between power and frequency (i.e., frequency analysis results) by analyzing signals from each sensor by a sound data analyzer in case of operating the image forming apparatus in an operating mode 1.
Figure 5B:
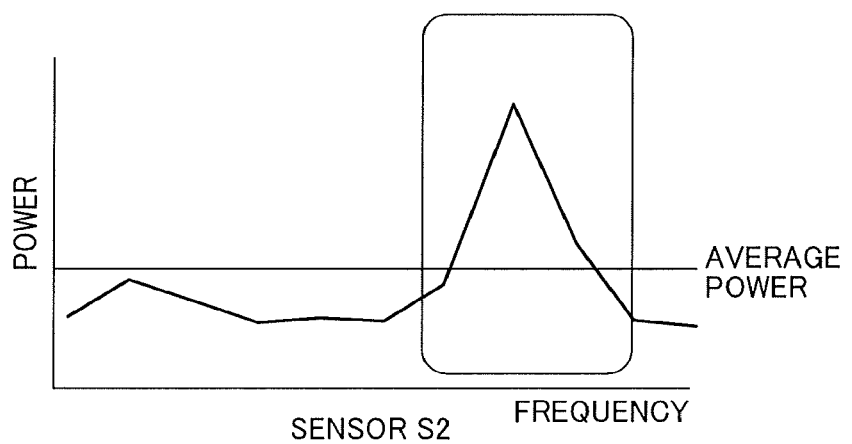
Figure 5C:
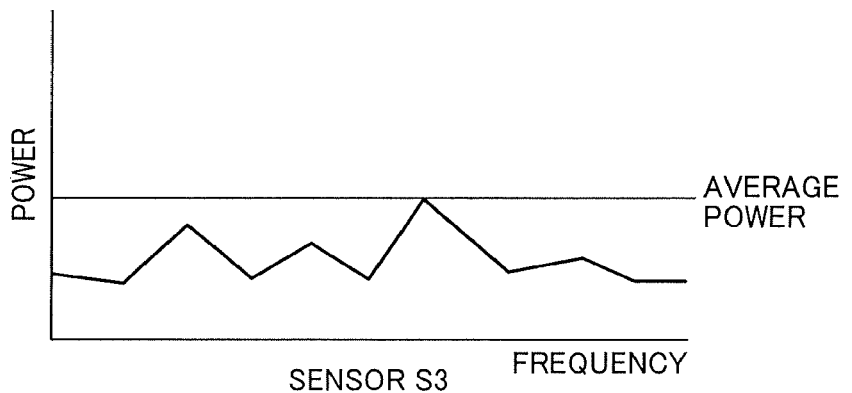

FIGS. 5A, 5B, and 5C are charts illustrating relationships between power and frequency (i.e., frequency analysis results) plotting frequency in the horizontal axis and power in the vertical axis by analyzing signals from each of the sensors S1 to S3 by the collected sound data analyzer 20a in case of operating the image forming apparatus 1 in operating mode 1.

As illustrated in FIGS. 5A to 5C, the most noticeable feature (surrounded by a frame) is observed in the sensor S2 in FIG. 5B. Here, the fact that a strong feature is observed indicates that the power is stronger than average power in comparison with overall average power (output). Each load such as the motor in the image forming apparatus 1 generates sound in the operation. Therefore, it is considered that a frequency band having a power stronger than the average power corresponds to a frequency band where sound is generated by the load. That is, it is assumed that a strong feature is observed in a part surrounded by broken lines in FIG. 5A. In addition, the fact that the strongest feature is observed indicates that its power is the strongest among the cases that a strong feature is observed. Ranges of the signals acquired by the sensors S1 to S3 are different with each other. Therefore, it is required to correct the data as needed to make it possible to compare data from the sensors S1 to S3 at a same scale.

As described above, in case of actually operating the image forming apparatus 1, if its operating mode is operating mode 1, abnormality is determined by using a signal from the sensor S2. In this method described above, it is assumed that the most noticeable variation is observed in the frequency band that the strong feature is observed if abnormality occurs.

Next, an operation of selecting the sensor S for each of operating mode 1, operating mode 2, and so on is described below.

Figure 6:
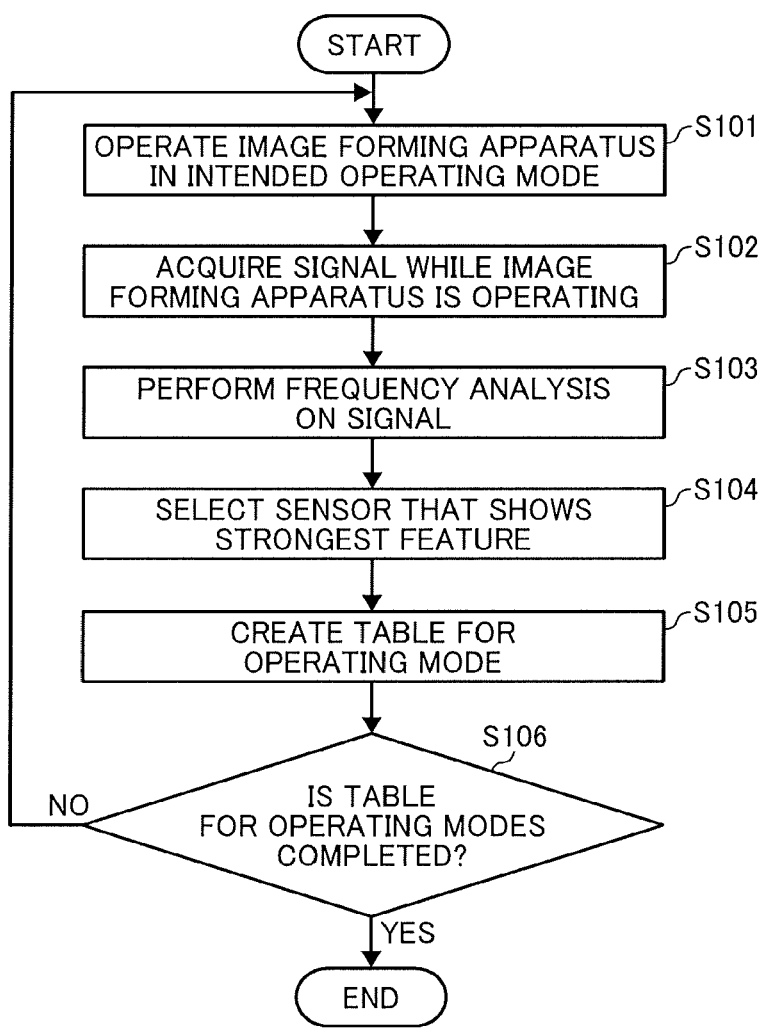
FIG. 6 is a flowchart illustrating an operation of selecting a sensor for each of a plurality of operating modes.

FIG. 6 is a flowchart illustrating an operation of selecting the sensor S for each of operating mode 1, operating mode 2, and so on, performed by the computer 2.

The computer 2 selects an operating mode to be performed, and causes the image forming apparatus 1 to operate in the selected operating mode in S101. Subsequently, the collected sound data analyzer 20a acquires signals during the operation using the sensors S1 to S3 in S102. The collected sound data analyzer 20a analyzes the signals acquired by the sensors S1 to S3 (i.e., power (sensor output) is examined for each frequency) in S103. The sensor selector 20d selects the sensor that the strongest feature is observed in S104.

Next, the table creator 20b generates a table for the selected operating mode in S105. At S106, the controller 20 determines whether a data field in the table is created for each of the operating modes, and if NO, the operation returns to S101 to select another operating mode to repeat S101 to S105. After completing generation of the data field in the table for each of the operating modes (YES in S106), the operation ends. The generated table is stored in the HDD 204 as a storage unit, as illustrated below.

TABLE 1

| Operating mode | Sensor to be used |
|---|---|
| Operating mode 1 | Sensor S2 |
| Operating mode 2 | Sensor S3 |
| Operating mode 3 | Sensor S1 |
| — | — |

Table 1 illustrates a table storing the sensor to be used for each of the operating modes generated as described above.

In this case, the sensor S to be used is selected for each operating mode.

That is, the sensor S2 is selected for operating mode 1, the sensor S3 is selected for operating mode 2, and the sensor S1 is selected for operating mode 3.

Next, an operation of determining abnormality using the result from the sensor S performed by the malfunction determination unit 20c is described below.

Figure 7:
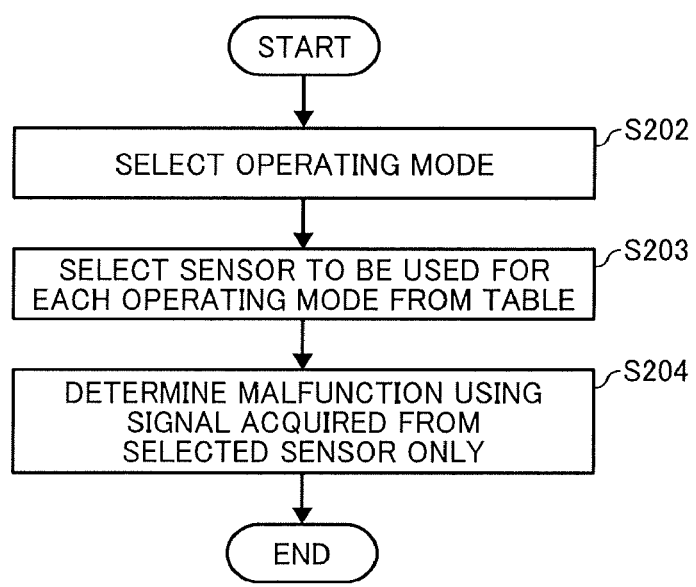
FIG. 7 is a flowchart illustrating an operation of determining abnormality performed by a malfunction determination unit using results from the sensor.

FIG. 7 is a flowchart illustrating an operation of determining abnormality performed by the malfunction determination unit 20c using the result from the sensor S. The operation of FIG. 7 is performed after the image forming apparatus 1 is turned on, for example. In this case, the computer 2 may turn on the image forming apparatus 1, or the image forming apparatus 1 is turned on by user operation.

The controller 20 in the computer 2 selects the operating mode from the table in the Table 1 in S202. The controller 20 selects the sensor S used in the selected operating mode from the table in Table 1 in S203. The malfunction determination unit 20c determines abnormality by using the signal acquired from the selected sensor S only in S204. After determining abnormality, the operation ends.

In this embodiment, the table is created so that only the sensor that the strongest feature is observed can be easily selected. However, the table may be generated to allow the computer 2 to select more than one sensor (such as all sensors) that output power larger than the average power by a predetermined amount.

Next, the second embodiment is described.

In this embodiment, after selecting one sensor S that is the most effective among three sensors S1 to S3, a range of the frequency band to be used for determination is further narrowed.

Compared to the first embodiment, this embodiment is able to acquire a signal whose S/N ratio improves. However, since information to be used is too focused, precision in determining abnormality may decrease compared to the first embodiment. Accordingly, it is desirable to select one of the methods depending on the situation to be used.

Figure 8:
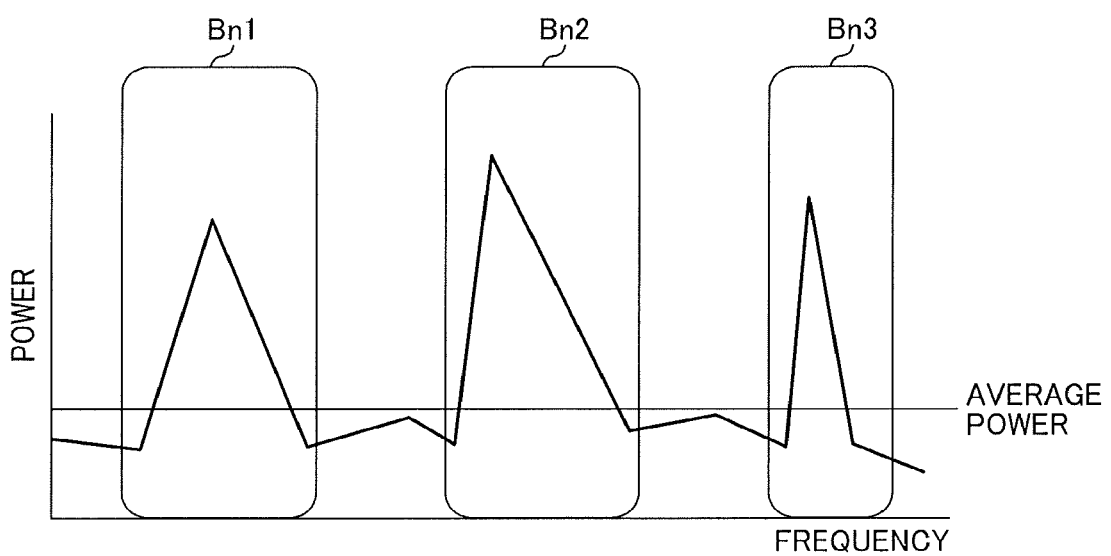
FIG. 8 is a chart illustrating a result of performing frequency analysis on an output of the selected sensor just like the case in FIG. 5, and FIGS. 9A and 9B are flowcharts illustrating an operation of selecting a band as an embodiment of the present invention.

FIG. 8 is a chart illustrating a result of performing frequency analysis on an output of the selected sensor S just like the case in FIGS. 5A to 5C.

An operation of narrowing down the frequency band to be used is described below with reference to FIG. 8.

In FIG. 8, strong features are observed in three frequency bands Bn1, Bn2, and Bn3 surrounded by frames.

In this case, the strong feature is defined just like the case in the first embodiment. As a result, only signals in these three frequency bands Bn1, Bn2, and Bn3 are used for determining abnormality.

In this embodiment, three frequency bands (parameters) are used. However, the number of used frequency bands is not limited to 3, and the number of frequency bands (parameters) may be arbitrarily set.

As described in the first embodiment before, in case of selecting all of the multiple sensors that output power larger than the average power by a predetermined amount, the operation described above is performed on all selected sensors.

Next, an operation of narrowing down the frequency band in this embodiment is described below.

Figure 9A:
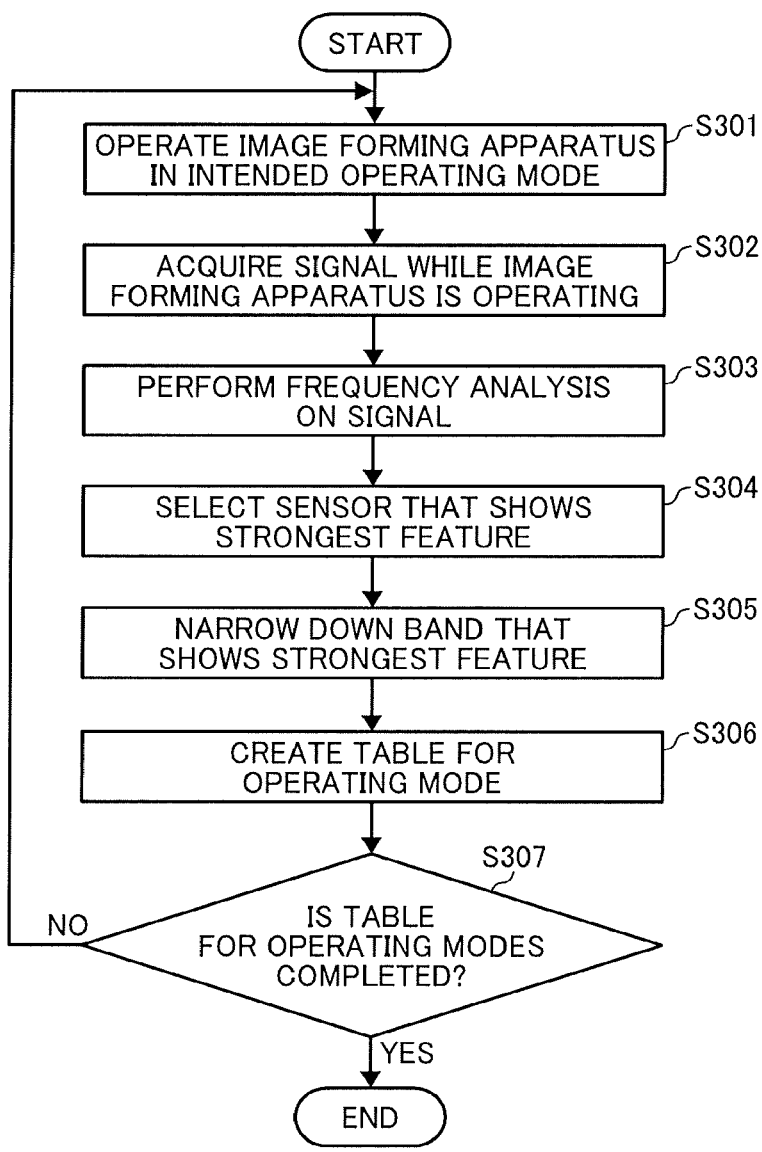
Figure 9B:
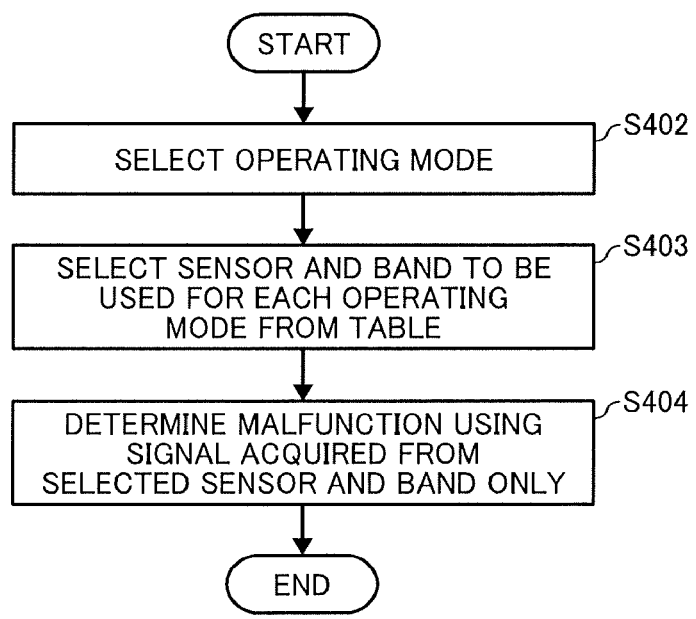

FIGS. 9A and 9B are flowcharts illustrating an operation of narrowing down a band in this embodiment.

In FIG. 9A, the computer 2 causes the image forming apparatus 1 to operate in a selected operating mode in S301, while selecting the sensor S obtained from the table for that operating mode. The computer 2 acquires the signal from the selected sensor S while the image forming apparatus 1 is operating (i.e., collected sound data) in S302. Subsequently, the computer 2 performs frequency analysis on the acquired signal in S303. The computer 2 selects the frequency band having the strongest feature observed in S304. After narrowing down a range of the frequency band to include the frequency band (for example, Bn1, Bn2, and Bn3 in FIG. 8) that strong feature is observed in S305, the computer 2 creates a data field in the table for the selected operating mode in S306. After completing the data fields in the table for each operating mode (YES in S307), the operation ends.

After completing the table for each operating mode, in FIG. 9B, if the image forming apparatus 1 is turned, the operating mode is extracted from the table as needed in S402. In this case, the computer 2 may turn on the image forming apparatus 1, or the image forming apparatus 1 is turned on by user operation as described before. Subsequently, the sensor and frequency band to be used is selected for each operating mode extracted from the table in S403. After determining abnormality using the signal acquired from the selected sensor and the frequency band only in S404, the operation ends.

TABLE 2

| Operating mode | Sensor to be used | Frequency band to be used |
|---|---|---|
| Operating mode 1 | Sensor S2 | 16 KHz to 18 KHz |
| Operating mode 2 | Sensor S3 | 300 KHz to 400 KHz |
|  |  | 500 KHz to 600 KHz |
| Operating mode 3 | Sensor S1 | 1 KHz to 2 KHz |
|  |  | 4 KHz to 5 KHz |
|  |  | 10 KHz to 11 KHz |
| — | — | — |

Table 2 illustrates an example of the table storing data for each operating mode.

In this case, the sensor S to be used and the frequency band to be used are illustrated for each operating mode.

That is, the sensor S2 and frequency band 16 KHz to 18 KHz are used for operating mode 1, the sensor S3 and frequency bands 300 KHz to 400 KHz and 500 KHz to 600 KHz are used for the operating mode 2, and the sensor S1 and frequency bands 1 KHz to 2 KHz, 4 KHz to 5 KHz, and 10 KHz to 11 KHz are used for operating mode 3.

As described above, by narrowing down frequency bands of sound data in determining abnormality, it is possible to determine abnormality more precisely compared to the case that uses all used frequency bands of the sound data.

In the embodiments, abnormality is detected using multiple kinds of sensors that may acquire different kinds of signals (i.e., air vibrations and solid vibrations etc.) and various frequency bands. As a result, since effective kinds of signal and frequency band are selected automatically, in order to enhance precision in detecting abnormality, it is possible to effectively utilize signals in effective frequency bands.

In the embodiments described above, the image forming apparatus is taken as an example of the target diagnosed apparatus. However, the target diagnosed apparatus is not limited to the image forming apparatus. The embodiments may be applied to any apparatus that operates in various operating modes and generates sound in accordance with the operation corresponding to the operating mode.

In addition, sound data described in the above embodiments is an example of physical data, and the physical data is not limited to the case described before. The physical data detected by a sensor also includes frequency of vibration and frequency of acceleration etc. For example, after detecting frequency of vibration in accordance with the operation or detecting frequency of acceleration along with the vibration, it is possible to acquire data indicating their physical quantities from a sensor and use the data.

In the above-described example embodiment, a computer can be used with a computer-readable program, described by object-oriented programming languages such as C++, Java (registered trademark), JavaScript (registered trademark), Perl, Ruby, or legacy programming languages such as machine language, assembler language to control functional units used for the apparatus or system. For example, a particular computer (e.g., personal computer, workstation) may control an information processing apparatus or an image processing apparatus such as image forming apparatus using a computer-readable program, which can execute the above-described processes or steps. In the above-described embodiments, at least one or more of the units of apparatus can be implemented as hardware or as a combination of hardware/software combination. The computer software can be provided to the programmable device using any storage medium or carrier medium for storing processor-readable code such as a floppy disk, a compact disk read only memory (CD-ROM), a digital versatile disk read only memory (DVD-ROM), DVD recording only/rewritable (DVD-R/RW), electrically erasable and programmable read only memory (EEPROM), erasable programmable read only memory (EPROM), a memory card or stick such as USB memory, a memory chip, a mini disk (MD), a magneto optical disc (MO), magnetic tape, a hard disk in a server, a solid state memory device or the like, but not limited these. Numerous additional modifications and variations are possible in light of the above teachings. It is therefore to be understood that within the scope of the appended claims, the disclosure of the present invention may be practiced otherwise than as specifically described herein.

For example, elements and/or features of different illustrative embodiments may be combined with each other and/or substituted for each other within the scope of this disclosure and appended claims.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

The invention claimed is:

1. A malfunction determining apparatus for determining a malfunction of a target apparatus, the malfunction determining apparatus comprising:
   a receiver to receive a plurality of items of physical data having frequency bands that are different from each other, the physical data being outputted by multiple sensors in the target apparatus while the target apparatus is operating in each one of a plurality of operating modes; and
   circuitry to:
      analyze the received physical data to identify, for each of the operating modes, at least one of the physical data having a specific feature from among the plurality of items of physical data that are received from the target apparatus,
      store in a memory, for each of the operating modes, information indicating at least one sensor of the multiple sensors that has outputted the at least one of the physical data that is identified, a first operating mode of the operating modes being associated with first information indicating a first sensor of the multiple sensors, a second operating mode of the operating modes being associated with second information indicating a second sensor of the multiple sensors, and a third operating mode of the operating modes being associated with third information indicating a third sensor of the multiple sensors,
      select the first operating mode of the operating modes, and
      determine an abnormality related to a physical quantity of the target apparatus operating in the selected first operating mode of the operating modes, using only the physical data output from the first sensor stored in the memory for the selected first operating mode, without using the physical data output from the second and the third sensors of the multiple sensors, wherein
   the circuitry analyzes a frequency of the received physical data to observe for the specific feature in the frequency, and stores the information indicating the at least one sensor that has outputted the physical data having the frequency in which the specific feature is observed.

2. The malfunction determining apparatus according to claim 1,
   wherein the circuitry analyzes a frequency of the received physical data to observe for the frequency having a power greater than an average power of all of the physical data received from the multiple sensors, and stores the information indicating the at least one sensor that has outputted the physical data having the frequency with the power greater than the average.

3. The malfunction determining apparatus according to claim 1,
   wherein the circuitry further analyzes a frequency of the at least one physical data that is identified as having the specific feature to extract at least one frequency band having the specific feature, and stores information indicating the at least one frequency band having the specific feature in the memory for the at least one physical data.

4. A malfunction determining system, comprising:
   the malfunction determining apparatus according to claim 1; and
   the target apparatus, the target apparatus including the multiple sensors that output the physical data having the frequency bands that are different from each other.

5. The malfunction determining apparatus according to claim 1, wherein
   the physical data is a sound, a vibration, or an acceleration.

6. A malfunction determining method for determining a malfunction of a target apparatus, the malfunction determining method comprising:
   receiving, from a target apparatus, a plurality of items of physical data having frequency bands that are different from each other, the physical data items being outputted by multiple sensors in the target apparatus while the target apparatus is operating in each one of a plurality of operating modes;
   analyzing the received physical data to identify, for each of the operating modes, at least one of the physical data items having a specific feature from among the plurality of items of physical data that are received from the target apparatus;
   storing in a memory, for each of the operating modes, information indicating at least one sensor of the multiple sensors that has outputted the at least one of the physical data item that is identified, a first operating mode of the operating modes being associated with first information indicating a first sensor of the multiple sensors, a second operating mode of the operating modes being associated with second information indicating a second sensor of the multiple sensors, and a third operating mode of the operating modes being associated with third information indicating a third sensor of the multiple sensors;

selecting the first operating mode of the operating modes; and determining an abnormality related to a physical quantity of the target apparatus operating in the selected first operating mode of the operating modes, using only the physical data outputted from the first sensor stored in the memory for the selected first operating mode, without using the physical data outputted from the second and the third sensors of the multiple sensors, wherein the analyzing includes analyzing a frequency of the received physical data to observe for the specific feature in the frequency, and the storing includes storing the information indicating the at least one sensor that has outputted the physical data having the frequency in which the specific feature is observed.

7. The malfunction determining method according to claim 6, wherein the analyzing includes analyzing a frequency of the received physical data to observe for the frequency having a power greater than an average power of all of the physical data received from the multiple sensors, and wherein the storing includes storing the information indicating the at least one sensor that has outputted the physical data having the frequency with the power greater than the average.

8. The malfunction determining method according to claim 6, wherein the analyzing includes analyzing a frequency of the at least one physical data that is identified as having the specific feature to extract at least one frequency band having the specific feature, and wherein the storing includes storing information indicating the at least one frequency band having the specific feature in the memory for the at least one physical data.

9. A non-transitory, computer-readable recording medium storing a program that, when executed by one or more processors of a malfunction determining apparatus, causes the processors to implement a malfunction determining method for determining a malfunction of a target apparatus, the malfunction determining method comprising:

receiving, from a target apparatus, a plurality of items of physical data having frequency bands that are different from each other, the physical data items being outputted by multiple sensors in the target apparatus while the target apparatus is operating in each one of a plurality of operating modes;

analyzing the received physical data to identify, for each of the operating modes, at least one of the physical data items having a specific feature from among the plurality of items of physical data that are received from the target apparatus;

storing in a memory, for each of the operating modes, information indicating at least one sensor of the multiple sensors that has outputted the at least one of the physical data item that is identified, a first operating mode of the operating modes being associated with first information indicating a first sensor of the multiple sensors, a second operating mode of the operating modes being associated with second information indicating a second sensor of the multiple sensors, and a third operating mode of the operating modes being associated with third information indicating a third sensor of the multiple sensors;

selecting the first operating mode of the operating modes; and determining an abnormality related to a physical quantity of the target apparatus operating in the selected first operating mode of the operating modes, using only the physical data output from the first sensor stored in the memory for the selected first operating mode, without using the physical data outputted from the second and the third sensors of the multiple sensors, wherein the analyzing includes analyzing a frequency of the received physical data to observe for the specific feature in the frequency, and the storing includes storing the information indicating the at least one sensor that has outputted the physical data having the frequency in which the specific feature is observed.

* * * * *